(12) United States Patent
Giersch et al.

(10) Patent No.: US 9,198,703 B2
(45) Date of Patent: Dec. 1, 2015

(54) SYSTEM FOR INSERTING A PIN INTO A SCREW

(75) Inventors: Helge Giersch, Laboe (DE); Ingo Bauer, Duesseldorf (DE); Jörg Mayer, Niederlenz (CH); Philipp Seiler, Arboldswil (CH)

(73) Assignees: Stryker Trauma GmbH (DE); Woodwelding AG (CH)

( * ) Notice: Subject to any disclaimer, the term of this patent is extended or adjusted under 35 U.S.C. 154(b) by 318 days.

(21) Appl. No.: 13/876,364

(22) PCT Filed: Sep. 30, 2010

(86) PCT No.: PCT/EP2010/064542
§ 371 (c)(1),
(2), (4) Date: Apr. 29, 2013

(87) PCT Pub. No.: WO2012/041376
PCT Pub. Date: Apr. 5, 2012

(65) Prior Publication Data
US 2013/0304135 A1    Nov. 14, 2013

(51) Int. Cl.
*A61B 17/88* (2006.01)
*A61B 17/86* (2006.01)
*A61B 17/74* (2006.01)
*A61B 17/00* (2006.01)

(52) U.S. Cl.
CPC ........... *A61B 17/864* (2013.01); *A61B 17/8872* (2013.01); *A61B 17/74* (2013.01); *A61B 17/8605* (2013.01); *A61B 17/865* (2013.01); *A61B 17/8822* (2013.01); *A61B 2017/00004* (2013.01)

(58) Field of Classification Search
USPC ................. 606/60, 86 A, 86 B, 86 R, 75, 99, 606/300–321, 331
See application file for complete search history.

(56) References Cited

U.S. PATENT DOCUMENTS

| 4,154,239 A | 5/1979 | Turley |
| 4,411,570 A | 10/1983 | Juric |
| 4,428,261 A | 1/1984 | Takatsu et al. |

(Continued)

FOREIGN PATENT DOCUMENTS

| EP | 2236101 A1 | 10/2010 |
| FR | 2445806 A1 | 8/1980 |

(Continued)

OTHER PUBLICATIONS

Bailey et al., "Biomechanical evaluation of a new composite bioresorbable screw", Journal of Hand Surgery (British and European Volume, 2006) 31 B: 2 : 208-212.

(Continued)

*Primary Examiner* — David Bates
*Assistant Examiner* — Samuel Hanna
(74) *Attorney, Agent, or Firm* — Lerner, David, Littenberg, Krumholz & Mentlik, LLP

(57) ABSTRACT

System for inserting an augmentation pin into an augmentation screw, comprising a pin inserter with an axial through-bore and a lateral opening, a pin-magazine with a pin-retainer for an augmentation pin, wherein the pin-magazine may be placed in the lateral opening of the pin-inserter and an augmentation pin in the pin-retainer may be aligned with the axial through-bore. The augmentation pin may be pushed by means of a pusher from the pin-magazine into an augmentation screw, when the augmentation screw is arranged in front of the pin-inserter.

13 Claims, 9 Drawing Sheets

(56) References Cited

U.S. PATENT DOCUMENTS

| | | | |
|---|---|---|---|
| 4,475,266 A | | 10/1984 | Suska |
| 4,569,469 A | * | 2/1986 | Mongeon et al. ............... 227/19 |
| 4,653,489 A | | 3/1987 | Tronzo |
| 4,929,239 A | | 5/1990 | Braun |
| 5,190,560 A | | 3/1993 | Woods et al. |
| 6,328,746 B1 | | 12/2001 | Gambale |
| 6,569,186 B1 | | 5/2003 | Winters et al. |
| 7,758,620 B2 | | 7/2010 | Porcher |
| 2004/0243139 A1 | | 12/2004 | Lewis et al. |
| 2005/0187559 A1 | | 8/2005 | Raymond et al. |
| 2006/0161161 A1 | * | 7/2006 | Shifrin et al. ................... 606/75 |
| 2007/0260250 A1 | | 11/2007 | Wisnewski et al. |
| 2007/0265622 A1 | | 11/2007 | Aeschlimann et al. |
| 2007/0271761 A1 | | 11/2007 | Haytayan |
| 2009/0088720 A1 | | 4/2009 | Oostman, Jr. |
| 2009/0163962 A1 | | 6/2009 | Dauster et al. |
| 2010/0076503 A1 | | 3/2010 | Beyar et al. |

FOREIGN PATENT DOCUMENTS

| | | |
|---|---|---|
| WO | 0007510 A1 | 2/2000 |
| WO | 2007073743 A1 | 7/2007 |
| WO | 2008096363 A2 | 8/2008 |
| WO | 2009132472 A2 | 11/2009 |
| WO | 2011054122 A1 | 5/2011 |

OTHER PUBLICATIONS

Fang et al., "Processing and mechanical properties of HA/UHMWPE nanocomposites", Biomaterials Jul. 2006; 27 (20):3701-3707.
Wintermantel und Suk-Woo Haa, "Medizinaltechnik mit biokomatiblen Materialien und Verfahren", 3. Auflage, Springer, Berlin 2002 (in the following referred to as "Wintermantel"), p. 200, for information on PGA and PLA see pp. 202 ff., on PCL see p. 207, on PHBUPHV copolymers p. 206; on polydioxanone PDS p. 209. p. 161 ff. (PE, Hostalen Gur 812, Höchst AG), pp. 164 ff. (PET) 169 ff. (PA, namely PA 6 and PA 66), 171 ff. (PTFE), 173 ff. (PMMA), 180 (PUR, see table), 186 ff. (PEEK), 189 ff. (PSU), 191 ff. (POM-Polyacetal, tradenames Delrin, Tenac, has also been used in endoprostheses by Protec).
Search report of PCT/EP2010/064542 dated May 31, 2011.
Written Opinion of PCT/EP2010/064542 dated May 31, 2011.
Wintermantel und Suk-Woo Haa, "Medizinaltechnik mit biokom atiblen Materialien und Verfahren", 3. Auflage, Springer, Berlin 2002 (in the following referred to as "Wintermantel"), p. 200, for information on PGA and PLA see pp. 202 ff., on PCL see p. 207, on PHBIPHV copolymers p. 206; on polydioxanone PDS p. 209. p. 161 ff. (PE, Hostalen Gur 812, Höchst AG), pp. 164 ff.(PET) 169 ff. (PA, namely PA 6 and PA 66), 171 ff. (PTFE), 173 ff. (PMMA), 180 (PUR, see table), 186 ff. (PEEK), 189 ff. (PSU), 191 ff. (POM-Polyacetal, tradenames Delrin, Tenac, has been used in endoprostheses by Protec).
Bailey et al., "Biomechanical evaluation of a new composite bioresorbable screw", Journal of Hand Surgery (British and European Volume, 2006) 31 B: 2: 208-212.
Bonfield et al., Materials World, vol. 5 No. 1:Jan. 18-20, 1997.
Fang et al., "Processing and mechanical properties of HA/UHMWPE nanocomposites", Biomaterials Jul. 2006; 27(20):3701-3707.
Huang et al., "Novel Porous Hydroxyapatite Prepared by Combining H2O2 Foaming with PU Sponge and Modified with PLGA and Bioactive Glass", Journal of Biomaterials Applications; 21(4):351-374, Apr. 2007.
Huang et al., "Synthesis and characterization of nano-HA/PA66 composites", Journal of Materials Science: Materials in Medicine 14(7):655-660, 2003.
International Search Report and Written Opinion for Application No. PCT/EP2012/000880 dated Nov. 7, 2012.
Juhasz et al., "Mechanical properties of glass-ceramic A-W-polyethylene composites: effect of filler content and particle size", Biomaterials, Mar. 2004; 25(6):949-955.
Rea et al., "Bioactivity of ceramic-polymer composites with varied composition and surface topography", Journal of Materials Science: Materials in Medicine 15 (2004) 997-1005.

* cited by examiner

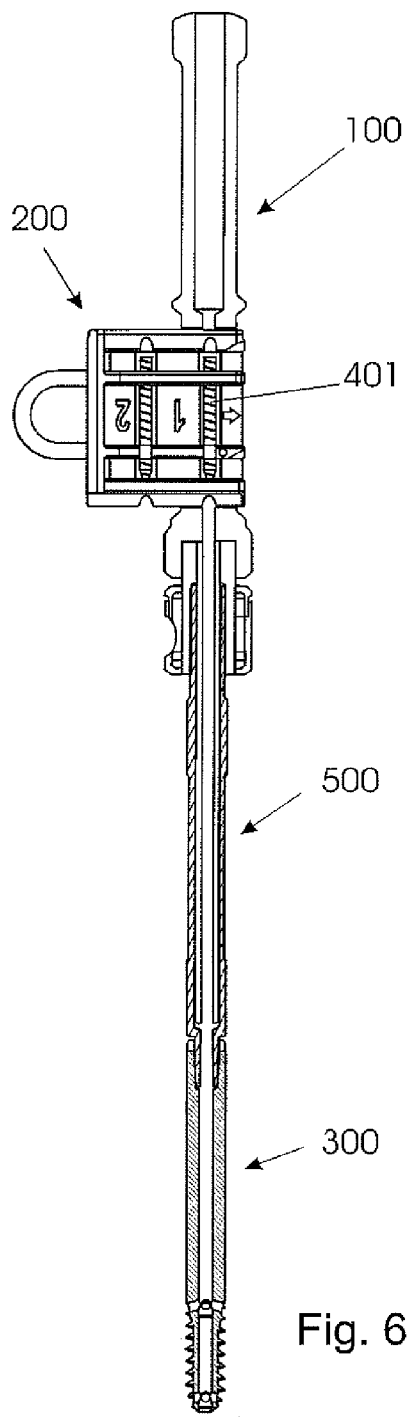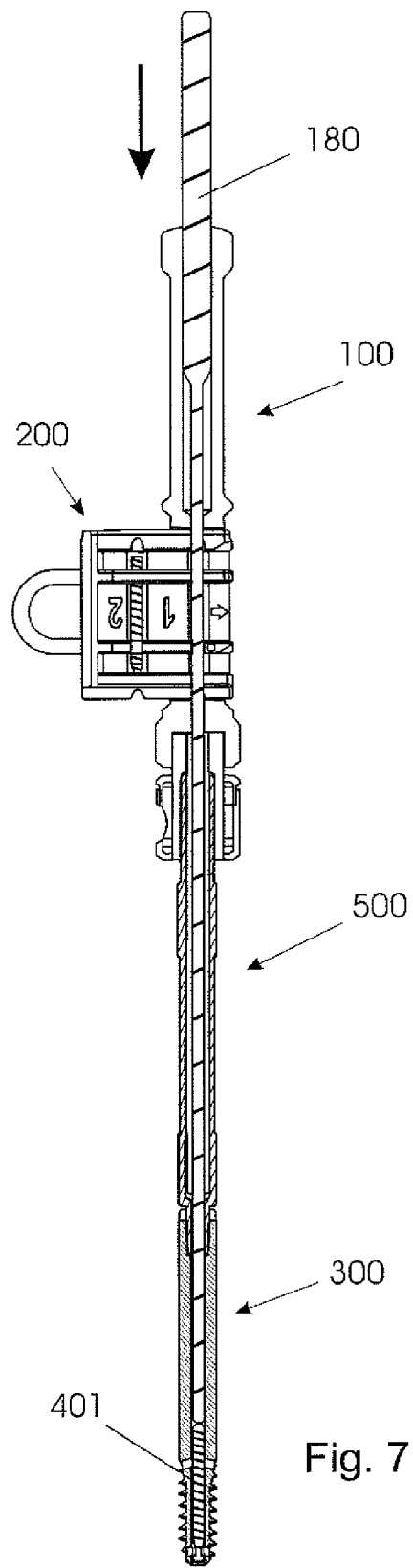
Fig. 6
Fig. 7

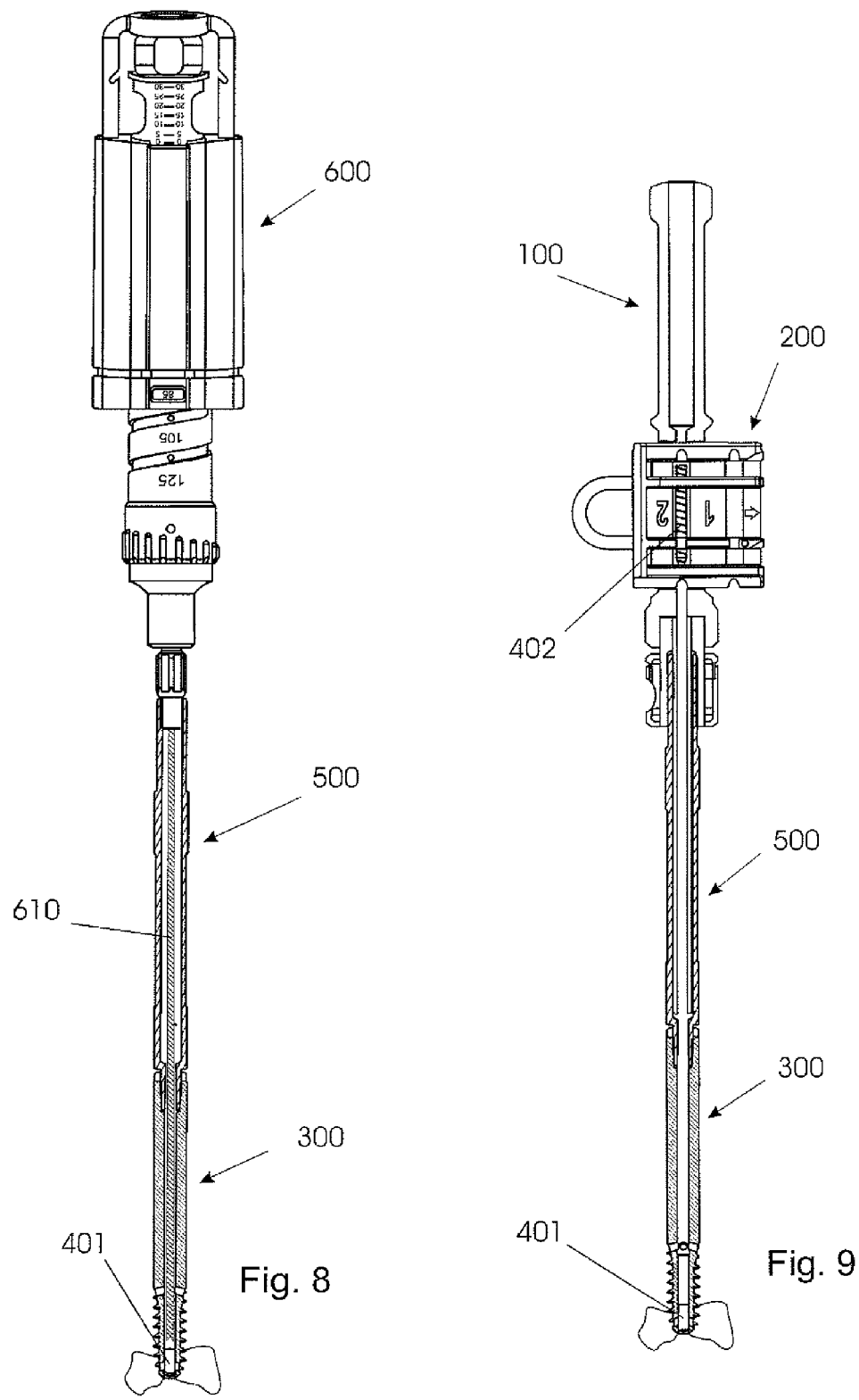

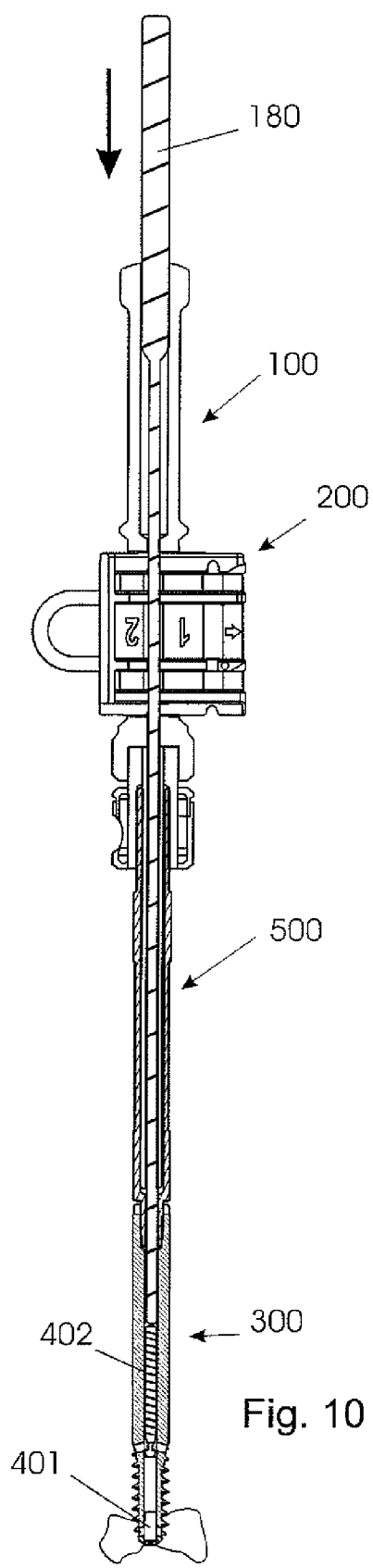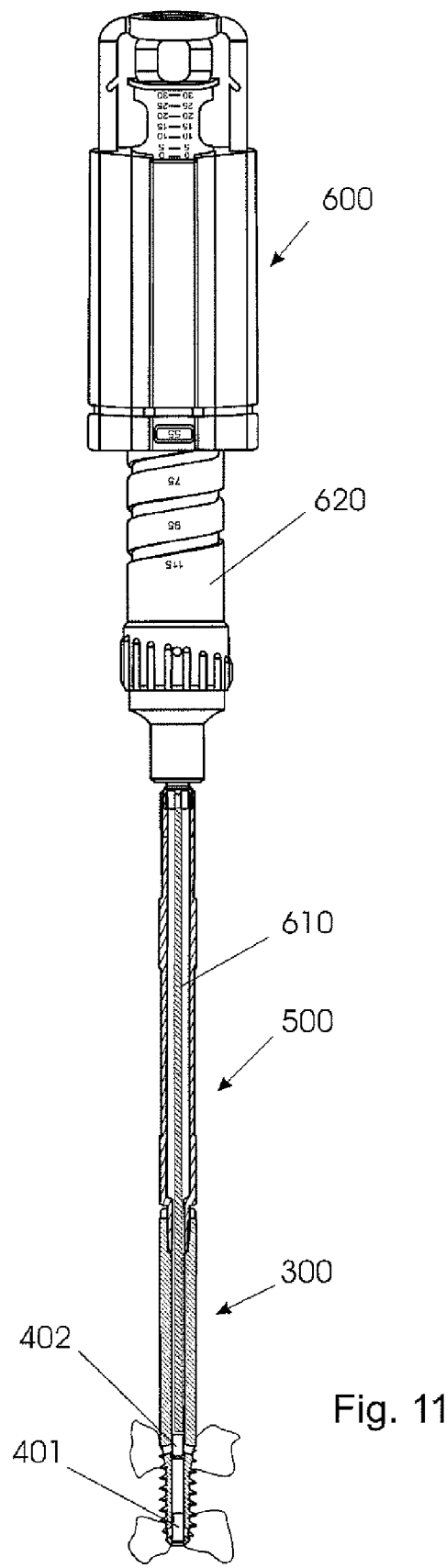
Fig. 10
Fig. 11

SYSTEM FOR INSERTING A PIN INTO A SCREW

CROSS-REFERENCE TO RELATED APPLICATION

The present application is a national phase entry under 35 U.S.C. §371 of International Application No. PCT/EP2010/064542 filed Sep. 30, 2010, published in English, incorporated herein by reference.

BACKGROUND OF THE INVENTION

The invention relates to a system for inserting a pin in a screw and augmenting the screw, including a pin-inserter, a pin-magazine, an augmentation screw and an augmentation pin. Furthermore, the invention relates to a method of use of the mentioned system.

Known from U.S. Pat. No. 4,653,489 is a system wherein fixation cement is introduced through a screw into a portion of a bone afflicted by osteoporoses. Femoral neck fractures as well as distal femoral fractures can be fixated by means of this device.

The system in accordance with prior art comprises a screw having a flow cavity, i.e. an axial through-bore through which bone cement can be introduced into the portion at the tip of the screw. The bone cement is advanced by a device which is releasably attached to the subsequent end of the screw. This device is similar to commercially available syringes. In use of this prior art device, the fixation cement is urged in an already fluidized state into the axial through-bore of the screw. Due to the pressure, the fixation cement is adequately fluidized, so that it can pass through the proximal end of the screw into the bone, as a result of which the screw is augmented in the bone.

This system has the drawback that the distribution of the fixation cement within the portion of the bone at the tip of the screw is neither reliable nor even.

SUMMARY OF THE INVENTION

An object of the invention may be to provide a system and a method by means of which a reliable and even augmentation of an augmentation screw in an installation site can be assured. This is achieved by the interrelated devices constituting a system in accordance with the invention. The devices are defined by the respective independent claims. Further embodiments are described in the dependent claims.

According to the invention, a pin-inserter for inserting an augmentation pin into an augmentation screw, comprises an elongated housing with an axial through-bore and a lateral opening which are connected to each other, and an elongated pusher which is movably and at least partially accommodated in the axial through-bore of the housing. An augmentation pin may be placed in the lateral opening aligned with the axial through-bore so that the augmentation pin may be moved by means of the pusher through the axial through-bore, out of the housing and into an augmentation screw.

Since the augmentation pin will usually be a small pin of approximately 3 cm to 4 cm, preferably of approximately 3.5 cm length and a few millimeters in diameter, such an augmentation pin will be reliably inserted into a augmentation screw by means of a pin-inserter in accordance with the invention.

It is noted, that the material of the polymer pin may be fluidizable and bio-compatible, wherein a bio-compatible material may be a material which does not negatively interfere with human or animal tissue. Additionally, the material may also be bio-absorbable.

The pusher according to the invention may have a length which is greater than a length of the axial through bore. Alternatively, the pusher may have a length which is shorter than the length of the axial through bore, wherein such a pusher may have a laterally extending grip portion which may protrude outwardly through a lateral slot provided in the housing of the pin-inserter.

For a stable fixation of the pin-inserter at an augmentation screw, the pin-inserter may further comprise a connection portion for fastening the housing of the pin-inserter at a proximal end of the augmentation screw, wherein the connection portion may include a quick-fastener.

In accordance with a further embodiment, the pin-inserter may further comprise a locking element for blocking a lateral movement of the augmentation pin, when the augmentation pin is placed in the lateral opening and is aligned with the axial through-bore.

The functionality of the pin-inserter may be further enhanced in that the lateral opening of the pin-inserter is a through-opening and a projection projects into this lateral opening, so that the augmentation pin is automatically aligned with the axial through-bore, when the augmentation pin is placed in the lateral opening and abuts the projection.

According to another embodiment of the invention, a pin-magazine with a pin-retainer for an augmentation pin may be utilized. The pin-magazine is adapted to be placed in the lateral opening of the housing of the pin-inserter and is adapted to align the augmentation pin with the axial through-bore in the housing of the pin-inserter, for inserting the augmentation pin into an augmentation screw. The pin-magazine is designed corresponding to the shape of the lateral opening in the housing of the pin-inserter in order to be placed in the lateral opening only with one orientation and direction.

The pin-magazine may further comprise a recess nearby or at the pin-retainer, so that on the one hand, when the pin-magazine is placed in the lateral opening of the housing, a projection at the housing protrudes into the recess, and on the other hand, when the augmentation pin is located in the pin-retainer, a portion of the augmentation pin is laterally exposed for an abutment at the projection. That is, an augmentation pin which is accommodated within the pin-retainer of the pin-magazine, may be easily handled and introduced from the site into the housing of the pin-inserter, wherein an abutment of the augmentation pin at a projection within the housing indicates the correct position of the pin-magazine as well as the augmentation pin inside the housing of the pin-inserter. An automatic alignment of the augmentation pin with the axial through-bore of the pin-inserter can thus be assured.

The pin-magazine may further comprise a notch into which a locking element of a pin-inserter may engage. By way of this, the pin-magazine may be fixated at a predetermined position and it may be avoided that the pin-magazine falls accidentally out of the pin-inserter.

In accordance with a further embodiment of the invention, an augmentation screw to be used with a pin-inserter and a pin-magazine as described above, comprises an axial bore for receiving an augmentation pin, the axial bore including a first step between a first section with a first diameter and a second section with a second diameter, and a second step between the second section and a third section with a third diameter, wherein the third diameter is greater than the second diameter which in turn is greater than the first diameter. At the second section and adjacent the first step, at least one first lateral bore is provided. At the third section and adjacent the second step, at least one second lateral bore is provided. Depending on the diameter of the augmentation pin, the augmentation pin may rest on the first step or the second step, when inserted into the axial bore of the augmentation screw. Having two steps in the axial bore provides the advantage that such a screw may be utilized in different applications by use of different and/or additional polymer pins.

The augmentation screw may further comprise a portion with an outer thread, wherein the first lateral bore as well as the second lateral bore are located in that portion.

In accordance with yet a further embodiment of the invention, the pin-magazine may comprise two pin-retainers, which may be adapted to hold two different pins. With this particular embodiment, an augmentation of for example a screw fixating a gamma nail may be realized in two steps. The difference of both pins will be a diverse diameter in a range of a 10 of a millimeter. Since this diverse diameters are not directly visible, it is necessary to use a tool to separate the pins.

Since the pin-magazine may fit only in one direction into the lateral opening of the pin-inserter, the two different pins located in the pin-retainers of the pin-magazine can only be introduced into the pin-inserter in a predetermined sequence. Thus, no mistake is possible by inserting the pins.

With the pusher, the augmentation pin may then be pushed into the axial bore of the augmentation screw. It is also possible to control the correct position of the pin after pushing. For this, respective marks may be provided at the proximal end portion of the pusher, which portion may be used for gripping the pusher and which will protrude from the proximal end of the pin-inserter housing.

The pin-magazine with the augmentation pins may be preserved in a sterile packaging. Because there may be a handle on the magazine, it would be not necessary to get in contact with the sterile pins.

The pin-inserter may be connected to a sleeve during the operation, which is adapted to the screw. The sleeve may be a tissue protection sleeve which is a kind of a lengthening piece, which may be suitable to facilitate the introduction of the screw into a bone, wherein muscles or other tissue surrounding the bone will complicate the attachment of an augmentation tool directly at the proximal end of the screw.

Beside the above-mentioned pin-inserter, pin-magazine, augmentation screw and augmentation pin, a system in accordance with an embodiment of the invention further comprises a tissue protection sleeve and an ultrasonic applicator. The tissue protection sleeve may be arranged between the augmentation screw and the connection portion of the pin-inserter, and the ultrasonic applicator may be capable of fluidizing the augmentation pin within the augmentation screw and pressing the fluidized material through at least one of the lateral bores out of the screw.

A description in more detail of the steps performed while using the system in accordance with the invention may be followed in conjunction with the detailed description of an exemplary embodiment below.

It has to be noted that embodiments of the invention are described with reference to different subject-matters. In particular, some embodiments are described with reference to method-type claims, whereas other embodiments are described with reference to apparatus-type claims, however, a person skilled in the art will gather from the above and the following description that, unless otherwise notified, in addition to any combination of features belonging to one type of subject-matter, also any combination of features relating to different subject-matters is considered to be disclosed with this application.

The aspects defined above and further aspects, features and advantages of the present invention can also be derived from the examples of the embodiment to be described hereinafter and are explained with reference to examples of embodiments to which the invention is not limited.

BRIEF DESCRIPTION OF THE DRAWINGS

The invention will now be detailed by way of an exemplary embodiment with reference to the attached drawings.

FIGS. 6 to 11 show a sequence of conditions which appear during the use of the system according to the invention.

It is noted that the illustration in the drawings is only schematically and not to scale. In different figures, similar elements are provided with the same reference signs.

DETAILED DESCRIPTION OF AN EXEMPLARY EMBODIMENTS

Figure 1:
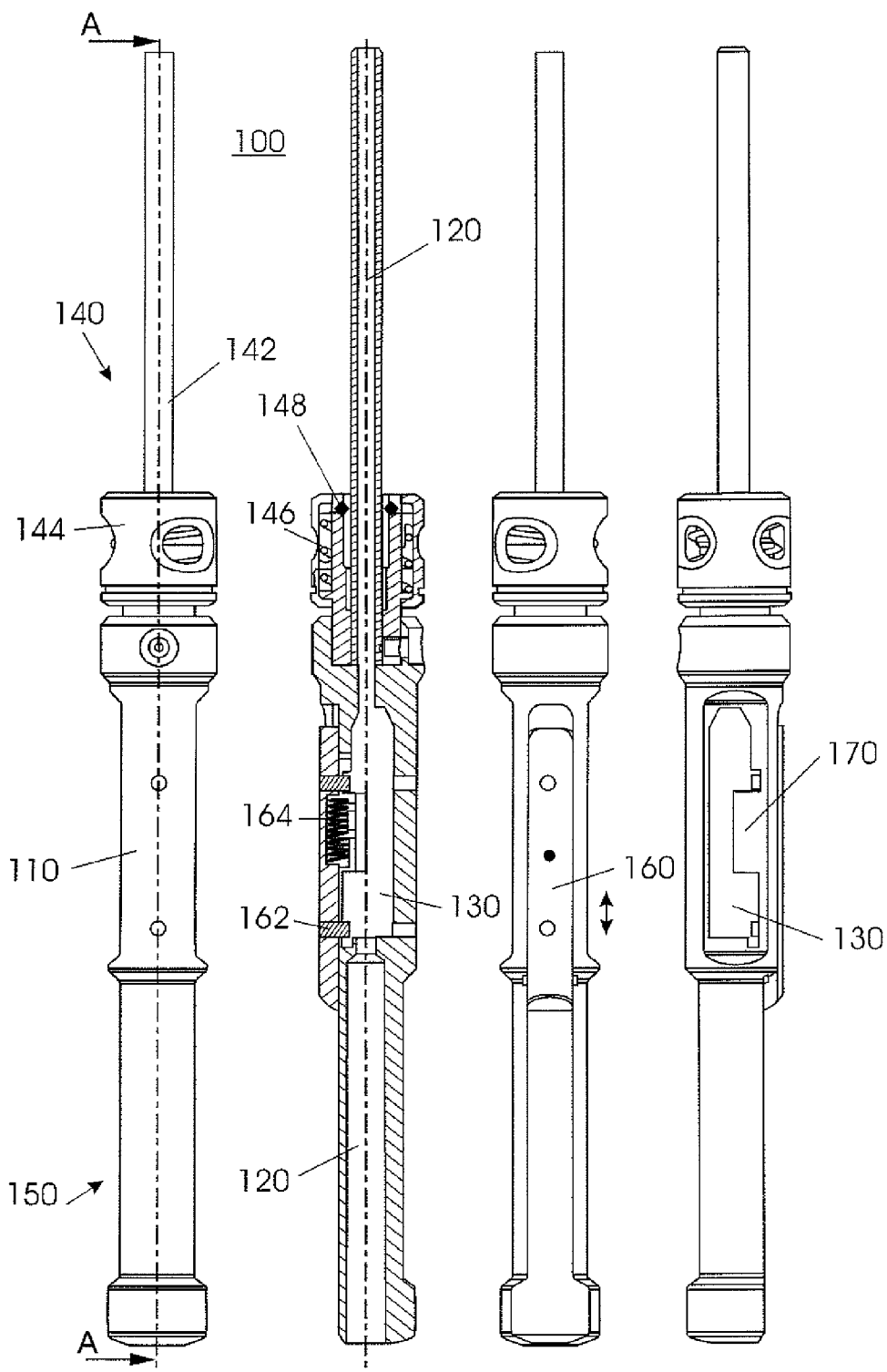
FIG. 1 shows three different side views and a section view of a pin-inserter according to the invention.

FIG. 1 shows, from left to right, a view from the bottom of a pin-inserter 100 according to the invention, a section view along the line A-A, a top view of the pin-inserter, and a side view of the pin-inserter.

The pin-inserter 100 includes a housing 110, an axial through-bore 120, a lateral opening 130, a connection portion 140, a grip portion 150, a locking element 160 and a projection 170.

The axial through-bore 120 formed in the housing 110 is provided with a step between a greater diameter and a smaller diameter. This step is formed adjacent and proximal to the lateral opening and the greater diameter of the axial through-bore is formed in the grip portion 150 of the housing 110. By way of this step, a correspondingly designed pusher may be moved within this axial through-bore 120, wherein the proximal end portion of the pusher may be easily handled.

The lateral opening 130 is asymmetrically shaped to assure that a pin-magazine which may be correspondingly formed, can be inserted into the lateral opening 130 only in one predetermined way.

The connection portion 140 includes a hollow shaft 142 which is adapted to be introduced into a tissue protection sleeve and which may guide an augmentation pin out of the pin-inserter and into an axial bore of an augmentation screw. A sleeve-like grip 144 is arranged at the connection portion 140, wherein this grip 144 is biased by a spring 146, so that the grip 144 may be shifted along the shaft 142 and will return to the starting position due to the spring force of the spring 146. By shifting the grip 144, engagement elements 148 may be released, so that an end of a tissue protection sleeve may be inserted into the grip 144, and the engagement elements 148 may engage corresponding notches or recesses at the tissue protection sleeve to fix the connection of the tissue protection sleeve with the pin-inserter.

The locking element 160 includes at least one locking pin 162 which protrude into the lateral opening 130 and which is adapted to engage in a notch formed at a pin-magazine to lock the pin-magazine within the lateral opening. Further the locking element 160 includes a spring 164 for biasing the locking element in a locking position. That is, a pin-magazine may only be inserted into the lateral opening 130, if the locking element 160 is moved against the force of the spring 164, for example by hand or by a structural element at the pin-magazine, when the pin-magazine is inserted into the lateral opening. The locking pin 162 may engage into the notch in the pin-magazine, when the locking element 160 is released. This will result in a locked positioning of the pin-magazine in the housing of the pin-inserter.

The projection 170 which is shown in accordance with this embodiment, projects from one side into the lateral opening 130. The projection 170 may be a substantially flat element, which provides an abutment for an augmentation pin, so that the augmentation pin will be reliably aligned with the axial through-bore 120 when the augmentation pin abuts at the projection.

Figure 2:
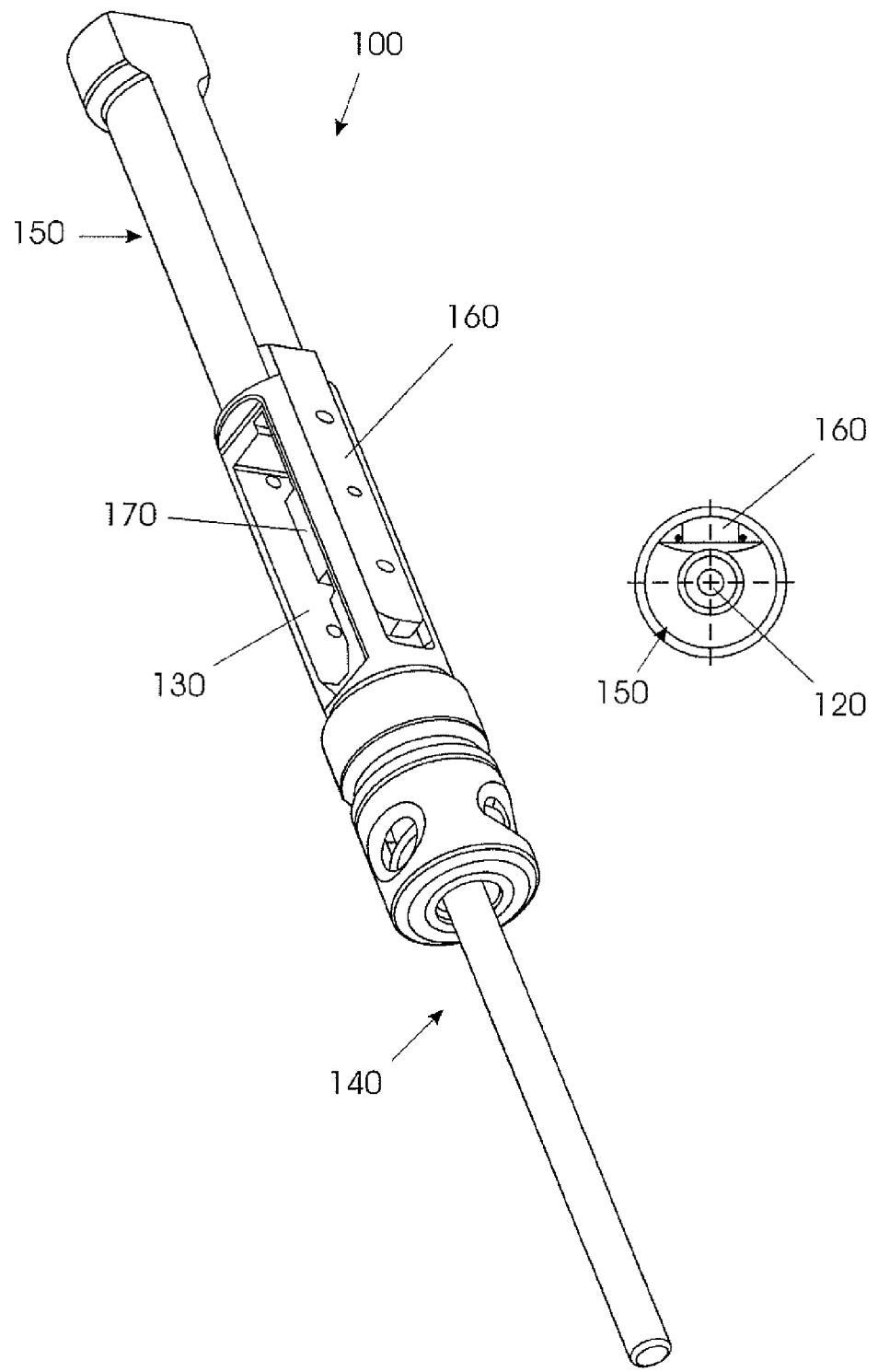
FIG. 2 shows an isometric view as well as a front view of the pin-inserter of FIG. 1.

FIG. 2 provides an isometric illustration of the pin-inserter according to the invention. Also in FIG. 2 the grip portion 150, the locking element 160, the projection 170, the lateral opening 130, and the connection portion 140 of the pin-inserter 100 is shown. As may be seen from the front view in FIG. 2, the axial through-bore 120 is formed at the center of the pin-inserter, according to this embodiment of the invention.

Figure 3:
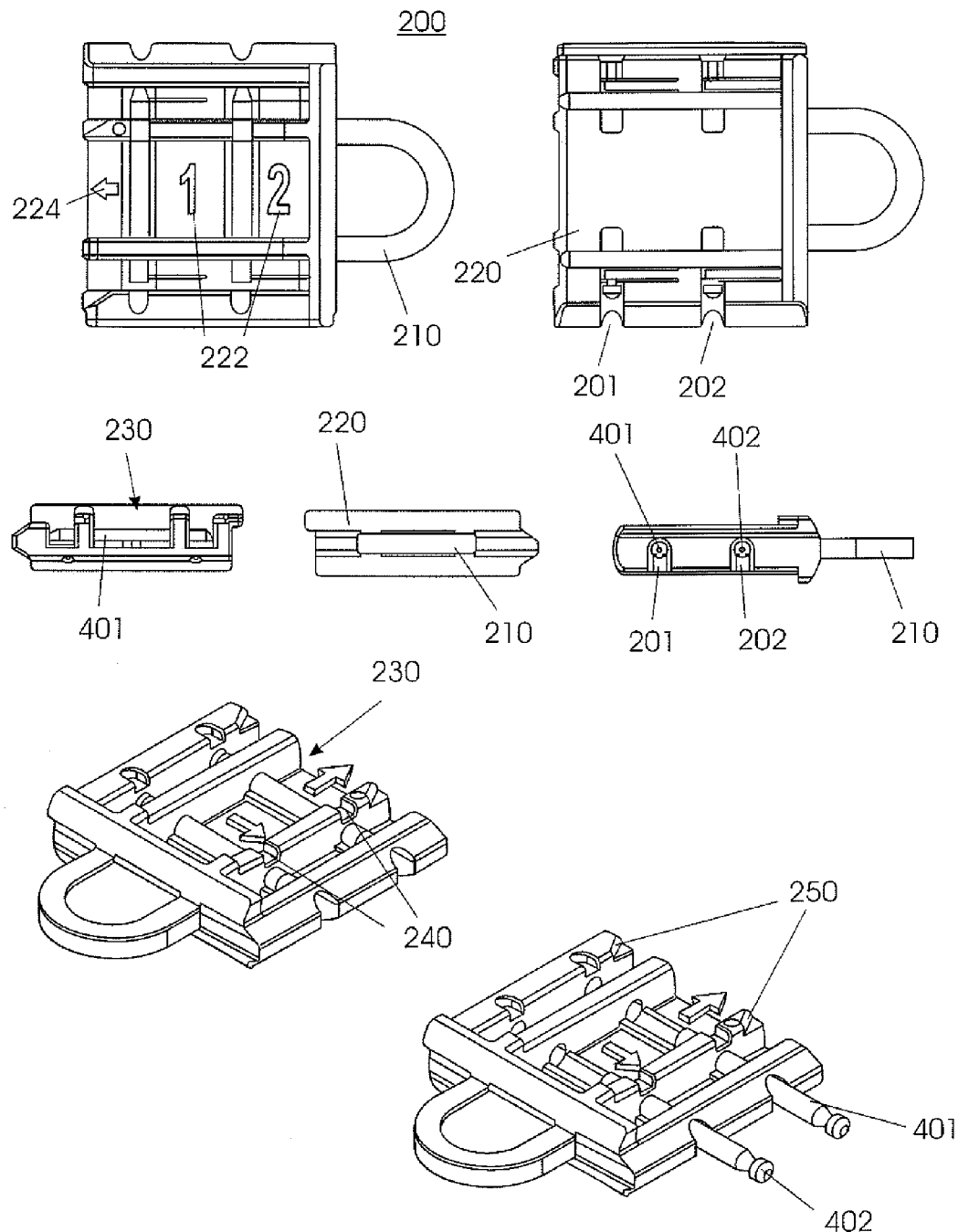
FIG. 3 shows side views, top and bottom views as well as isometric views of a pin-magazine according to the invention.

FIG. 3 shows several views of a pin-magazine 200 according to the invention. The pin-magazine 200 includes a grip portion 210, a body 220, and a recess 230. Transverse to the grip portion 210, two pin-retainers 201, 202 are formed. Each pin-retainer is realized by a sequence of recesses within and bores through the body 220 of the pin-magazine. A first pin-retainer 201 is formed at a position away from the grip portion 210, and a second pin-retainer 202 is formed nearby the grip portion 210.

By way of the distinct arrangement of the pin-retainers 201, 202 relative to the grip portion 210, it can be assured, that the pin-magazine 200 will be inserted into the lateral opening of the pin-inserter in a correct way, when the pin-magazine is gripped at the grip portion 210.

In the body 220 of the pin-magazine 200, notches 240 are formed, which are provided for an engagement with respective locking pins of the locking element of the pin-inserter. Such locking pins may be press to a side by means of chamfers 250 provided at the body 220, so that the locking element may be passively actuated when the pin-magazine is inserted into the lateral opening of the pin-inserter.

Further, signs may be provided at the body, indicating for example a direction 224 for an insertion of the magazine into the pin-inserter, or numbers 222 referring to the sequence for the augmentation pins.

In FIG. 3, also augmentation pins 401, 402 are visualized within the pin-retainers 201, 202.

Figure 4:
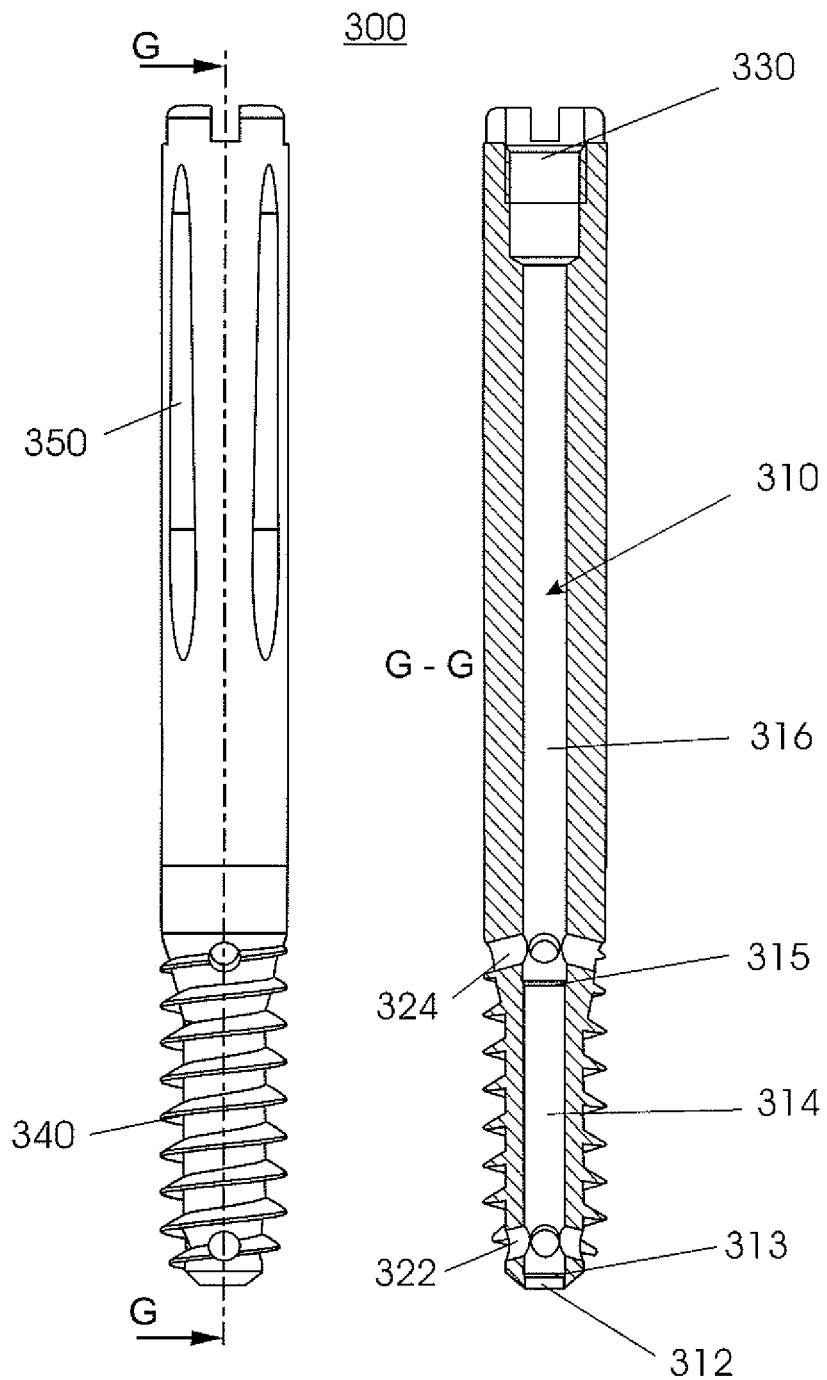
FIG. 4 shows a side view as well as a section view of an augmentation screw according to the invention.

FIG. 4 shows a side view of an augmentation screw 300 and a cross section view along the line G-G showing details of the axial bore inside the augmentation screw 300.

The axial bore 310 of the augmentation screw 300 is shown as a through bore including a first section 312, a first step 313, a second section 314, a second step 315 and a third section 316. The diameter of the first section 312 is smaller than the diameter of the second section 314 and the diameter of the second section 314 is smaller than the diameter of the third section 316. Near the first step 313 and in the second section 314, first lateral bores 322 are formed. Near the step 315 and in the third section 316, second lateral bores 324 are formed.

Furthermore, the augmentation screw 300 comprises an inner thread portion at a proximal end portion 330, an outer thread 340 at the distal end portion and grooves 350 in the outer surface of the shaft of the augmentation screw 300.

The inner thread at the proximal end portion 330 may be used for a connection with a screw driving tool and/or a tissue protection sleeve. The outer thread 340 may provide a first fixation of the augmentation screw in, for example, a bone. The positions of the first lateral bores 322 and the second lateral bores 324 is such that the distal end of the outer thread 340 and the proximal end of the outer thread 340 may be substantially surrounded by the material of the augmentation pin after a fluidization of the same. The material which is pressed out the lateral bores may thus provide a reliable augmentation at two portions of the augmentation screw within, for example, a bone.

The grooves 350 may be elongated and flat depressions. Such grooves may be used for a locking of rotational movements of the augmentation screw when the screw is positioned in a bone nail, for example a gamma nail. In such a situation, a locking screw may engage one of the grooves 350.

Figure 5:
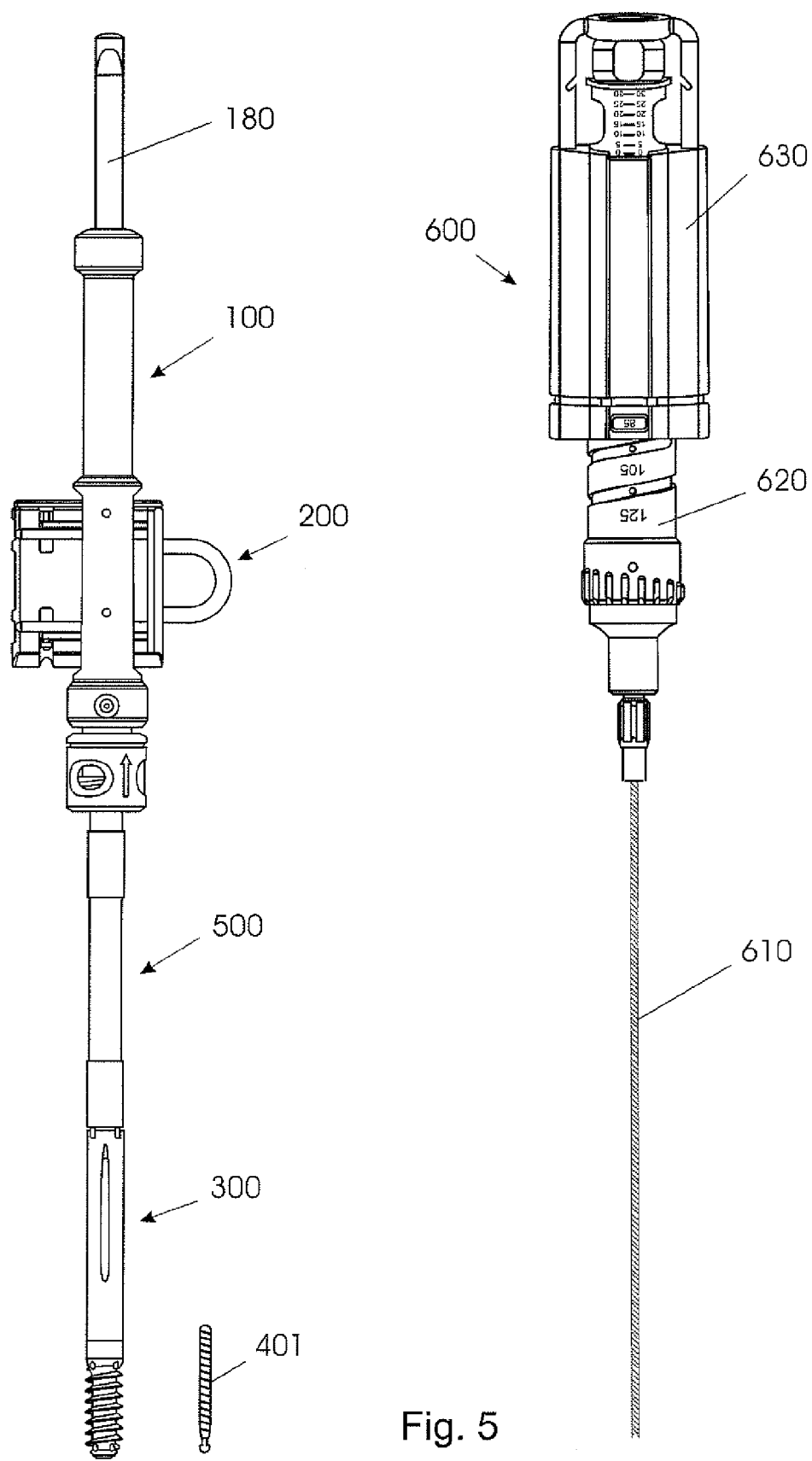
FIG. 5 illustrates a system for inserting and augmenting an augmentation screw according to the invention.

FIG. 5 illustrates exemplary embodiments of all elements which are part of a system in accordance with the invention. The system includes a pin-inserter 100 with a pusher 180, a pin-magazine 200, an augmentation screw 300, and an augmentation pin 401. Between the augmentation screw 300 and the pin-inserter 100, a tissue protection sleeve 500 is located. As may be seen in conjunction with the description of the method below, instead of the pin-inserter 100 an ultrasonic applicator 600 may be connected with the proximal end of the tissue protection sleeve 500. The ultrasonic applicator 600 includes a sonotrode 610, an adjusting portion 620 for adjusting the length of the ultrasonic applicator and a grip portion 630. The interrelation of the ultrasonic applicator 600 with the rest of the system will be described in the following.

With respect to the FIGS. 6 to 11, a sequence of conditions appearing during a use of the system according to the invention is illustrated.

In FIG. 6, a pin-inserter 100 with a pin-magazine 200 is connected to a tissue protection sleeve 500 which in turn is connected to an augmentation screw 300. Here, the pin-magazine 200 is positioned relative to the pin-inserter 100 such that a first augmentation pin 401 is aligned with the axial through-bore in the pin-inserter 100. It is noted, that the projection provided in the lateral opening, prevents a further introduction of the pin-magazine into the lateral opening, as long as the first augmentation pin is located in the pin-magazine, since the first augmentation pin may abut at the projection and thus block such a further introduction.

In FIG. 7, the first augmentation pin 401 is pushed by means of the pusher 180 out of the first pin-retainer of the pin-magazine 200 through the axial through-bore of the pin-inserter 100, through the tissue protection sleeve 500 and till the augmentation pin 401 abuts at the first step within the axial bore of the augmentation screw 300.

In FIG. 8, the pin-inserter 100 is removed from the tissue protection sleeve 500 and the ultrasonic applicator 600 is connected to the proximal end of the tissue protection sleeve 500. The length of the ultrasonic applicator 600 is adjusted such that the sonotrode 610 abuts at the proximal end of the augmentation pin 401. In FIG. 8, the material of the augmentation pin 401 is already fluidized and pressed out of the tip portion of the augmentation screw 300.

In FIG. 9, the pin-inserter 100 is again connected with the tissue protection sleeve 500, but with the pin-magazine 200 in a position such that a second augmentation pin 402 is aligned with the axial through-bore in the pin-inserter 100. The augmentation screw 300 at the distal end of the tissue protection sleeve 500 is further on augmented at the tip by the material of the first augmentation pin 401.

In FIG. 10, the second augmentation pin 402 is pushed by the pusher 180 till the second augmentation pin 402 rests on the second step in the axial bore of the augmentation screw 300. As in FIG. 7, the pusher 180 is moved with the augmentation pin in front of the tip of the pusher, in direction of the arrow through the pin-inserter 100, the pin-magazine 200 and the tissue protection sleeve 500.

In FIG. 11, the second augmentation pin 402 is fluidized by means of the ultrasonic applicator 600, i.e. by the sonotrode 610 of the ultrasonic applicator 600, and pressed out of the second lateral bores in the augmentation screw 300. For a fluidization of the second augmentation pin 402, the length of the ultrasonic applicator 600 is accordingly adjusted by the adjusting portion 620. As may be seen in comparison with FIG. 8, the adjusting portion is now longer.

Figure 12:
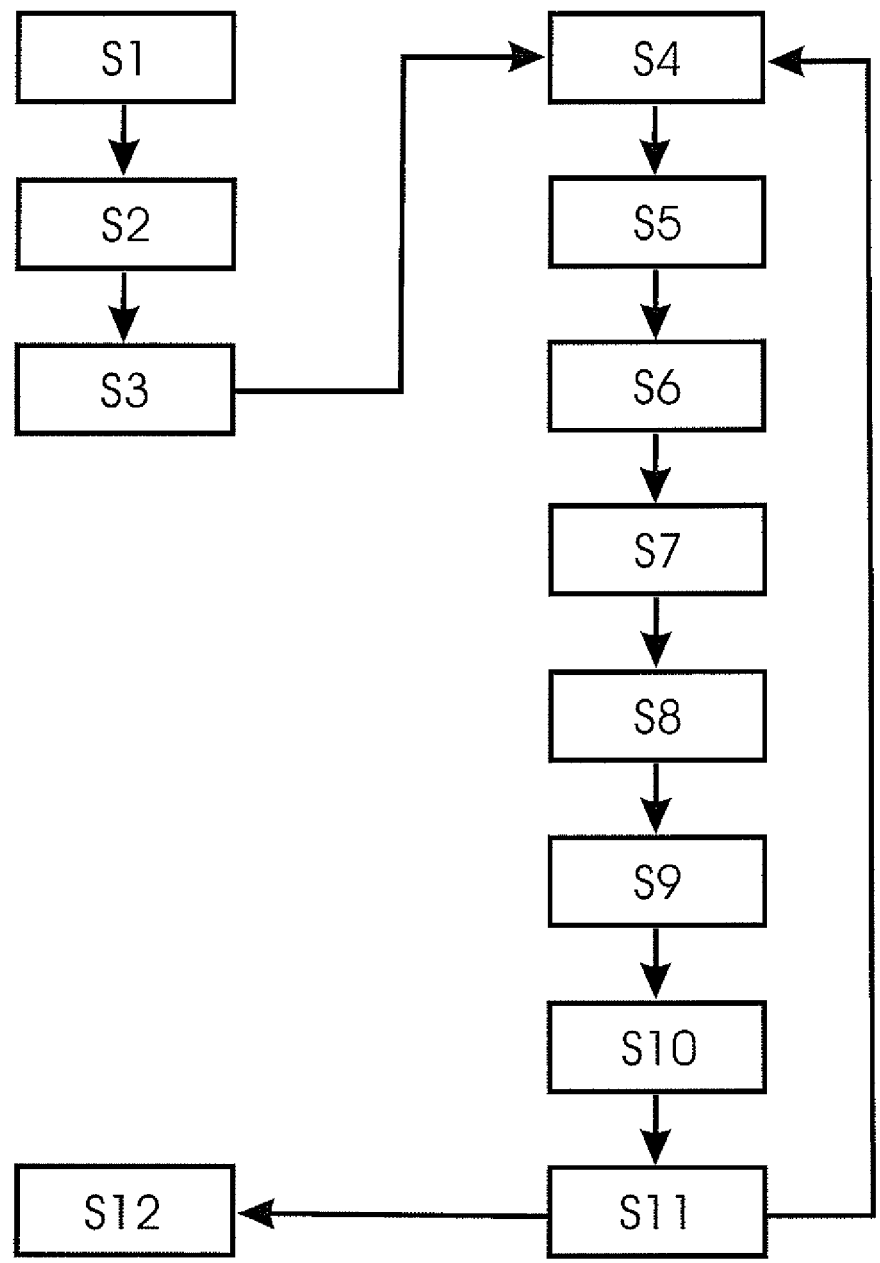
FIG. 12 show a flow-chart illustrating a method according to the invention.

The flow-chart in FIG. 12 illustrates the principles of using the system according to the invention. It will be understood that the steps described with respect to the method, and also with respect to FIGS. 6 to 11, are major steps, wherein these major steps might be differentiated or divided into several sub-steps. Furthermore, there might be also sub-steps between these major steps. Therefore, a sub-step is only mentioned if that step may be important for the understanding of the principles of the method according to the invention.

In step S1, a screw is introduced or implanted at an installation site. Particularly, it may be an augmentation screw which is implanted protruding through a transverse bore in a gamma nail.

In step S2, a tissue protection sleeve is fastened at the proximal end of the augmentation screw.

In step S3, a screw driver which may also be used for an implantation of the augmentation screw itself, will be removed from the tissue protection sleeve.

In step S4, the distal end, i.e. the connection portion of a pin-inserter, is connected to the proximal end of the tissue protection sleeve.

In step S5, a pin-magazine with at least one augmentation pin is placed within the lateral opening of the housing of the pin-inserter so that one augmentation pin is aligned with an axial through-bore in the pin-inserter. This alignment may be achieved by an abutment of the augmentation pin at a projection protruding into the lateral opening in the pin-inserter.

In step S6, the augmentation pin is pushed out of the pin-magazine by means of the pusher, through the pin-inserter and into the augmentation screw.

In step S7, the pin-inserter is removed from the tissue protection sleeve.

In step S8, the length of an ultrasonic applicator, particularly the length of a sonotrode protruding from the housing of the ultrasonic applicator, is adjusted to fit with the distance between the proximal end of the tissue protection sleeve and the proximal end of the augmentation pin inside the augmentation screw.

In step S9, the ultrasonic applicator is connected with the proximal end of the tissue protection sleeve so that the sonotrode tip is in contact with the proximal end of the augmentation pin.

In step S10, ultrasonic vibrations together with a predetermined force is applied by the sonotrode to the augmentation pin so that the material of the augmentation pin is fluidized and pressed out of lateral bores of the augmentation screw.

In step S11, the ultrasonic applicator is removed from the proximal end of the tissue protection sleeve.

If more than one augmentation pin should be utilized, the method steps S4 to S11 will be repeated, which is illustrated by the arrow going from step S11 back to step S4.

After the fluidization of all augmentation pins, in step S12, the tissue protection sleeve will be removed from the proximal end of the augmentation screw.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practising the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures can not be used to advantage. Any reference signs in the claims should not be construed as limiting the scope.

LIST OF REFERENCE SIGNS

100 Pin-inserter
110 Housing
120 Axial through-bore
130 Lateral opening
140 Connection portion
142 Hollow shaft
144 Grip
146 Elastic element
148 Engagement element
150 Grip portion
160 Locking element
162 Locking pin
164 Spring
170 Projection
180 Pusher
200 Pin-magazine
201,202 Pin-retainer
210 Grip portion
220 Body
230 Recess
240 Notch
250 Chamfer
300 Augmentation screw
310 Axial bore
312 First section
313 First step
314 Second section
315 Second step
316 Third section
322 First lateral bore
324 Second lateral bore
330 Proximal end portion
340 Outer thread
350 Groove
401,402 Augmentation pin
500 Tissue protection sleeve
600 Ultrasonic applicator
610 Sonotrode
620 Adjusting portion
630 Grip portion

The invention claimed is:

1. A system for inserting an implant into bone, comprising:
a plurality of polymeric augmentation pins;
an augmentation screw having an internal bore for receiving one of the augmentation pins;
a pin inserter having an elongated housing with an axial through-bore and a lateral opening, wherein the axial through-bore and the lateral opening are in communication with each other, and an elongated pusher which is movably and at least partially accommodated in the axial through-bore, so that, when one of the augmentation pins is placed in the lateral opening and is aligned with the axial through-bore, then the augmentation pin can be moved by means of the pusher through at least a portion of the axial through-bore, out of the housing and into the internal bore of the augmentation screw;
wherein the housing further comprises a connection portion for fastening a proximal end of the augmentation screw at the connection portion of the housing, such that the axial through-bore of the housing is coaxial with the internal bore of the augmentation screw;
wherein the lateral opening in the housing is a through-opening and wherein the housing further comprises a projection projecting into the lateral opening, so that one of the augmentation pins is blocked from lateral movement and is automatically aligned with the axial through-bore, when the one augmentation pin is placed in the lateral opening and abuts the projection;
the system further comprising a pin-magazine for holding the plurality of augmentation pins wherein the pin-magazine is designed to be at least partially received in the lateral opening of the housing; and wherein the polymeric augmentation pins are capable of being fluidized by ultrasonic energy.

2. The system of claim 1, wherein a length of the elongated pusher is greater than a length of the axial through-bore.

3. The system of claim 1, wherein the connection portion includes a releasable coupling for selective engagement with the proximal end of the augmentation screw.

4. The system of claim 1 wherein the pin-magazine is adapted to align a pin-retainer with the axial through-bore of the elongated housing, for inserting the augmentation pin into an augmentation screw, when the augmentation pin is located in the pin-retainer.

5. The system of claim 4, further comprising a recess formed on the pin-retainer, so that, when the pin-magazine is placed in the lateral opening of the housing, the projection on the housing protrudes into the recess, and, when the augmentation pin is located in the pin-retainer, a portion of the augmentation pin is laterally exposed for abutting the projection.

6. The system of claim 4 wherein the pin magazine further comprises a notch adapted for an engagement with a locking element of a pin-inserter.

7. The system of claim 4, wherein the pin-magazine comprises two pin-retainers.

8. The system of claim 7, wherein the two pin-retainers are adapted to hold two different pins.

9. A system for inserting an implant into bone, comprising:
a plurality of polymeric augmentation pins;
an augmentation screw having an internal bore for receiving one of the augmentation pins;
a pin inserter having an elongated housing with an axial through-bore and a lateral opening, wherein the axial through-bore and the lateral opening are in communication with each other, and an elongated pusher which is movably and at least partially accommodated in the axial through-bore, so that, when one of the augmentation pins is placed in the lateral opening and is aligned with the axial through-bore, then the augmentation pin can be moved by means of the pusher through at least a portion of the axial through-bore, out of the housing and into the augmentation screw; wherein the housing further comprises a connection portion for fastening a proximal end of the augmentation screw at the connection portion of the housing, such that the axial through-bore of the housing is coaxial with the internal bore of the augmentation screw;
wherein the lateral opening in the housing is a through-opening and wherein the housing further comprises a projection projecting into the lateral opening, so that the augmentation pin is blocked from lateral movement and is automatically aligned with the axial through-bore, when the augmentation in is placed in the lateral opening and abuts the projection;
the system further comprising a pin-magazine for holding the plurality of augmentation pins wherein the pin-magazine is designed to be at least partially received in the lateral opening of the housing;
wherein the polymeric augmentation pins are capable of being fluidized by ultrasonic energy; and
a tissue protection sleeve having a proximal end releasably coupled to a connection portion of the housing.

10. The system as set forth in claim 9, wherein the tissue protection sleeve releasably engages the proximal end of the augmentation screw.

11. The system of claim 9, wherein the connection portion includes a releasable coupling for selective engagement with the proximal end of the augmentation screw.

12. The system of claim 9 wherein the pin-magazine is adapted to align a pin-retainer with the axial through-bore of the elongated housing, for inserting the augmentation pin into an augmentation screw, when the augmentation pin is located in the pin-retainer.

13. The system of claim 12, further comprising a recess formed on the pin-retainer, so that, when the pin-magazine is placed in the lateral opening of the housing, the projection on the housing protrudes into the recess, and, when the augmentation pin is located in the pin-retainer, a portion of the augmentation pin is laterally exposed for abutting the projection.

* * * * *